United States Patent
Voege

[19]

[11] Patent Number: 6,155,258

[45] Date of Patent: Dec. 5, 2000

[54] OXYGEN DELIVERY SYSTEM

[76] Inventor: John S. Voege, 10521 Bishop Cir., Carmel, Ind. 46032

[21] Appl. No.: 09/257,113

[22] Filed: Feb. 25, 1999

[51] Int. Cl.[7] ........................................................ A62B 7/00
[52] U.S. Cl. ............................... 128/205.21; 128/205.25
[58] Field of Search ........................ 128/204.23, 204.18, 128/204.26, 204.27, 204.29, 205.21, 205.22, 205.24, 205.25, 207.11, 206.21, 206.23, 206.28, 206.29; 137/541, 613; 222/336, 5, 6

[56] References Cited

U.S. PATENT DOCUMENTS

| | | | |
|---|---|---|---|
| 3,180,524 | 4/1965 | Shepard et al. | 222/5 |
| 3,976,063 | 8/1976 | Henneman et al. | 128/142.7 |
| 4,221,216 | 9/1980 | Kranz | 128/201.23 |
| 4,241,896 | 12/1980 | Voege | 251/206 |
| 4,366,947 | 1/1983 | Voege | 251/206 |
| 4,606,340 | 8/1986 | Ansite | 128/205.24 |
| 4,664,108 | 5/1987 | Ansite | 128/202.26 |
| 4,802,472 | 2/1989 | Jung | 128/204.18 |
| 4,887,591 | 12/1989 | Okumura | 128/205.21 |
| 5,076,267 | 12/1991 | Pasternack | 128/205.22 |
| 5,273,185 | 12/1993 | Sacarto | 222/5 |
| 5,429,125 | 7/1995 | Wagner et al. | 128/205.25 |
| 5,443,062 | 8/1995 | Hayes | 128/204.26 |
| 5,488,946 | 2/1996 | Calhoun et al. | 128/205.21 |
| 5,662,100 | 9/1997 | Fox et al. | 128/205.24 |
| 5,690,100 | 11/1997 | Pomerantz | 128/205.24 |

*Primary Examiner*—Aaron J. Lewis
*Assistant Examiner*—Teena Mitchell
*Attorney, Agent, or Firm*—Johnson, Smith, Pence & Heath, LLP

[57] ABSTRACT

An oxygen delivery system provides supplemental oxygen on demand from an oxygen source to a human being via an oxygen mask. The system includes a regulator having an inlet and an outlet. The regulator is removably secured to the oxygen source. A release pin is disposed in the regulator for quickly actuating operation of the regulator. Prior to operation, the release pin maintains the regulator in a closed position so that the regulator prevents the flow of oxygen from the oxygen source. Upon removal of the release pin, the regulator assumes an open position so that it permits the flow of oxygen from the oxygen source, through the regulator, and to the human being. The system is rechargeable and may be carried on the person or stored at home for emergency use.

7 Claims, 3 Drawing Sheets

OXYGEN DELIVERY SYSTEM

BACKGROUND

The present invention pertains to pressure regulators and more particularly pertains to an oxygen delivery system for delivering oxygen on demand from an oxygen source to a human being via an oxygen mask.

Supplemental oxygen is often provided to individuals suffering from pulmonary diseases such as emphysema, bronchitis, and asthma. Supplemental oxygen can also be part of a post-operative regime where it is key to a patient's good health and speedy recovery. Most supplemental oxygen delivery systems operate alike.

Oxygen is delivered from an oxygen source, usually a tank containing pressurized fluid, through a regulator device and to the patient by way of a nasal cannula or face mask. Such devices, however, require professional care and attention to insure proper hook-up and operation. Another problem with present supplemental oxygen delivery systems is that the regulators have complicated pneumatic control systems for regulating the flow of oxygen. These include valves, solenoids, electronic sensors, and diaphragms, each of which adds significantly to manufacturing costs making mass production and sale of these devices cost-prohibitive. Moreover, regulator components become worn over time and may fail to operate. This is unacceptable.

Many of the same problems with oxygen delivery systems heretofore available make them clumsy and impossible to carry on the person as well. Elderly patients having reduced lung function must ride in battery powered carts due to the large oxygen tanks and delivery systems that require electricity to operate.

Another problem is that present oxygen delivery apparatus do not provide for immediate delivery of oxygen in emergency situations where time is of the essence. A time of need may include heart attack, stroke, or a smoke-filled home. Thus, there is a need for an oxygen delivery system, or kit, for use when one is away from the hospital or at home.

Home health care providers and patients could also benefit from a handy, easy-to-operate emergency oxygen delivery system capable of delivering oxygen on demand without the use of electric power. Clearly, an oxygen delivery system of this sort should be portable, reusable, and inexpensive to manufacture.

Therefore, it is highly desirable to provide a new oxy,ten delivery system.

It is highly desirable to provide a new oxygen delivery system that is easy to operate and that does not require a medical technician to hook-up.

It is also highly desirable to provide a new oxygen delivery system that does not include complicated pneumatic control systems with valves, solenoids, electronic sensors, and diaphragms that may wear out or fail to operate.

It is also highly desirable to provide a new oxygen delivery system that does not need a source of electricity to operate.

It is also highly desirable to provide a new oxygen delivery system capable of delivering oxygen instantly upon demand from an oxygen source to a human being.

It is also highly desirable to provide a new oxygen delivery system that is convenient to carry on the person and is inexpensive to manufacture and use repeatedly.

It is finally highly desirable to provide a new oxygen delivery system that meets all of the above desired features.

SUMMARY

It is an object of the invention to provide a new oxygen delivery system.

It is also an object of the invention to provide a new oxygen delivery system that is easy to operate and that does not require a medical technician to hook-up.

It is another object of the invention to provide a new oxygen delivery system that does not include complicated pneumatic control systems with valves, solenoids, electronic sensors, and diaphragms that may wear out or fail to operate.

It is yet another object of the invention to provide a new oxygen delivery system that does not need a source of electricity to operate.

It is still another object of the invention to provide a new oxygen delivery system capable of delivering oxygen instantly upon demand from an oxygen source to a human being.

It is also an object of the invention to provide a new oxygen delivery system that is convenient to carry on the person and is inexpensive to manufacture and use repeatedly.

It is finally an object of the invention to provide a new oxygen delivery system that meets all of the above desired features.

In the broader aspects of the invention there is provided an oxygen delivery system for delivering oxygen on demand from an oxygen source to a human being via an oxygen mask. The oxygen delivery system includes a hollow body with a top, a bottom, and an interior wall. The interior wall has a bottom surface, and an outlet bore extends through the interior wall.

A first spacer member is sealingly and slidingly positioned within the body. A release pin bore for retaining a release pin extends through the body between the top and the first spacer member. A central bore extends axially through the bottom for providing fluid communication between the oxygen source and the interior of the body. The central bore has an inlet.

A second spacer member is sealingly positioned on the bottom of the hollow body. The second spacer member has an axial bore extending through it.

A metering member is slidingly and sealingly disposed within the body between the first and second spacer members and is axially slidable between a closed position where the metering element seats on the inlet, thereby preventing the flow of oxygen from the source, and an open position where the metering element moves off of the inlet permitting the flow of oxygen from the source into the body.

DRAWINGS

The above-mentioned and other features and objects of the invention and the manner of attaining them will become more apparent and the invention itself will be better understood by reference to the following description of an embodiment of the invention taken in conjunction with the accompanying drawings wherein.

DESCRIPTION

Figure 1:
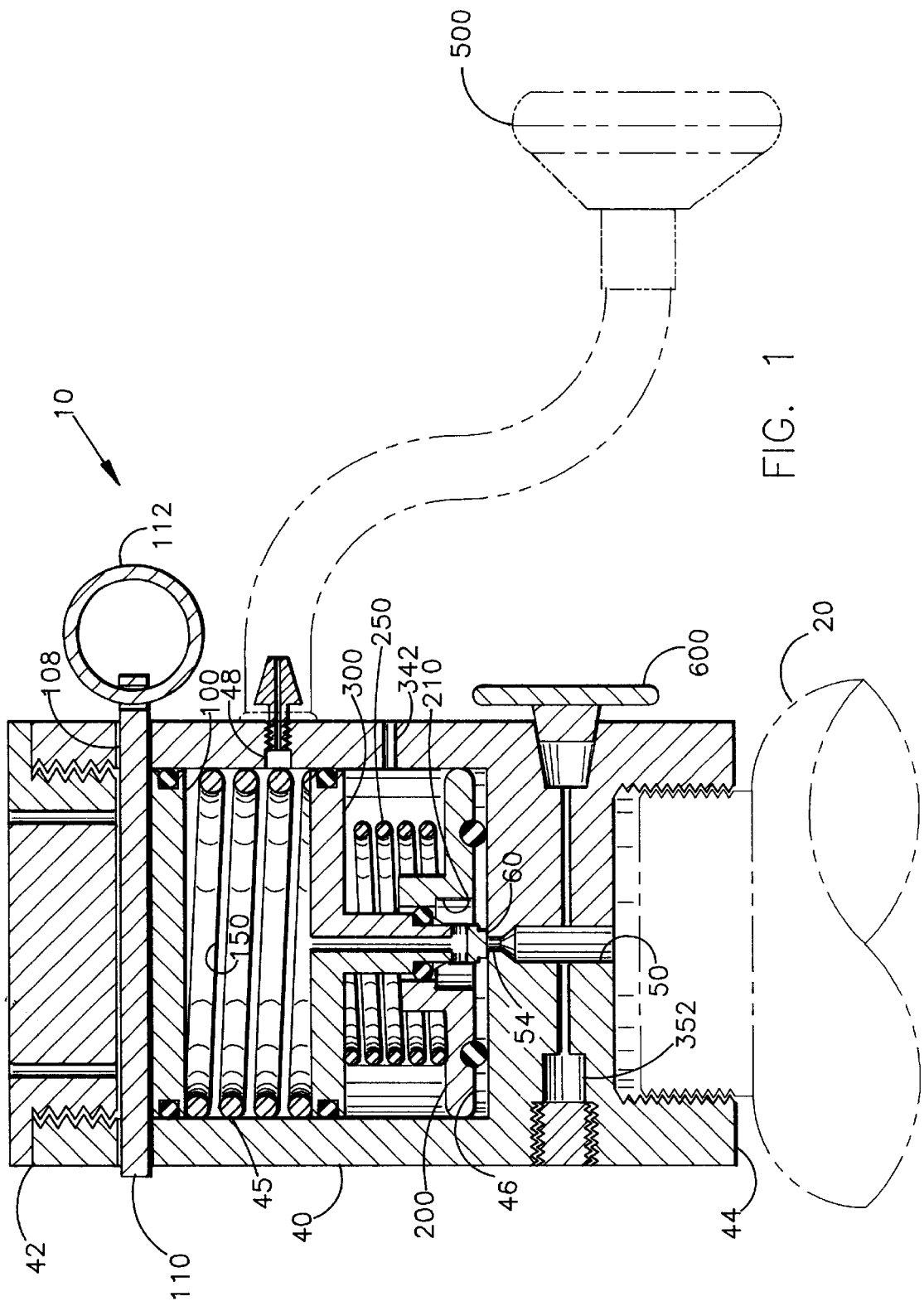
FIG. 1 is a partial cross-sectional view of an embodiment of the invention showing the regulator in its closed position.
Figure 2:
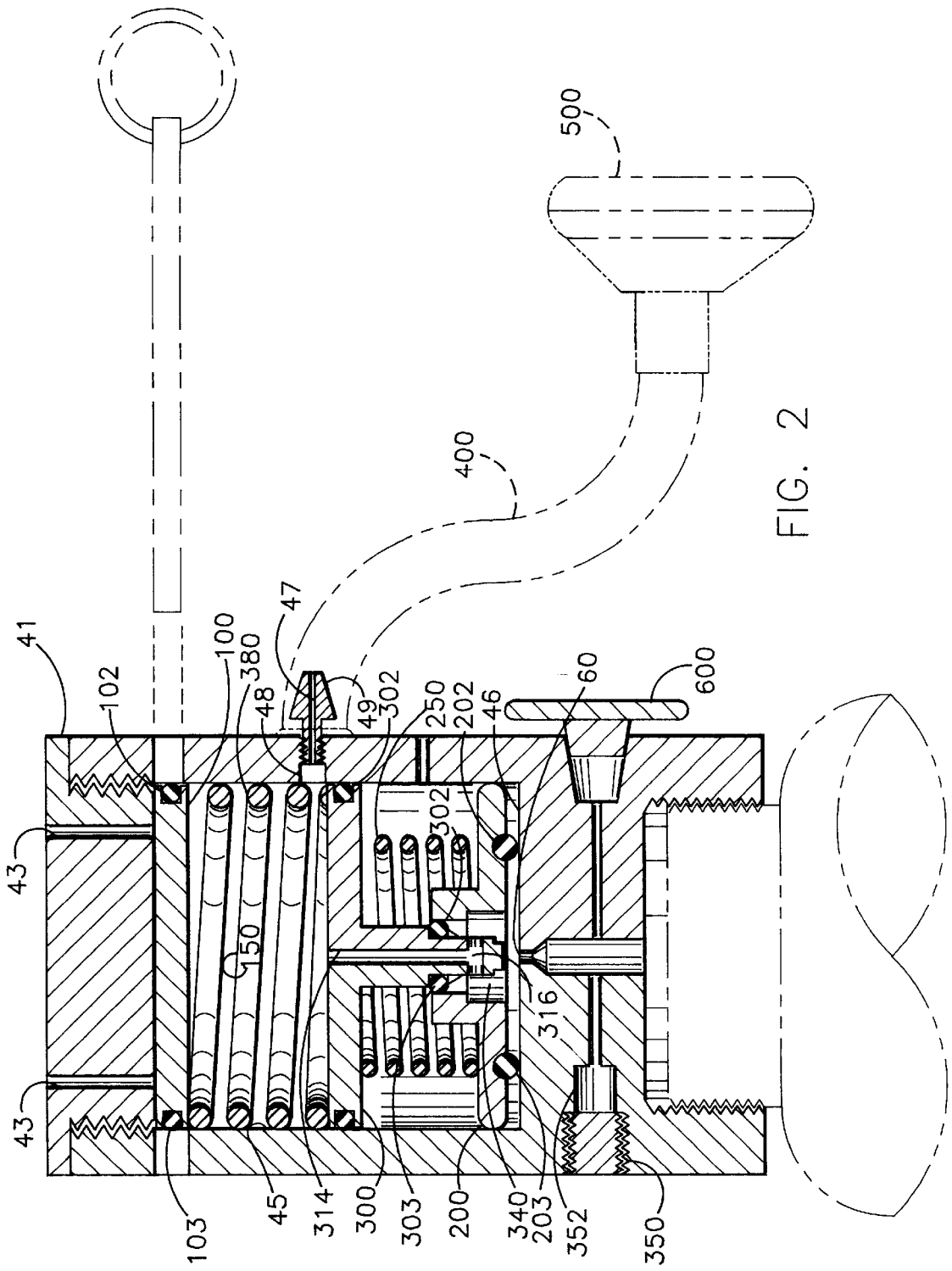
FIG. 2 is also a partial cross-sectional view of the invention showing the regulator in its open position with the release pin removed.
Figure 3:
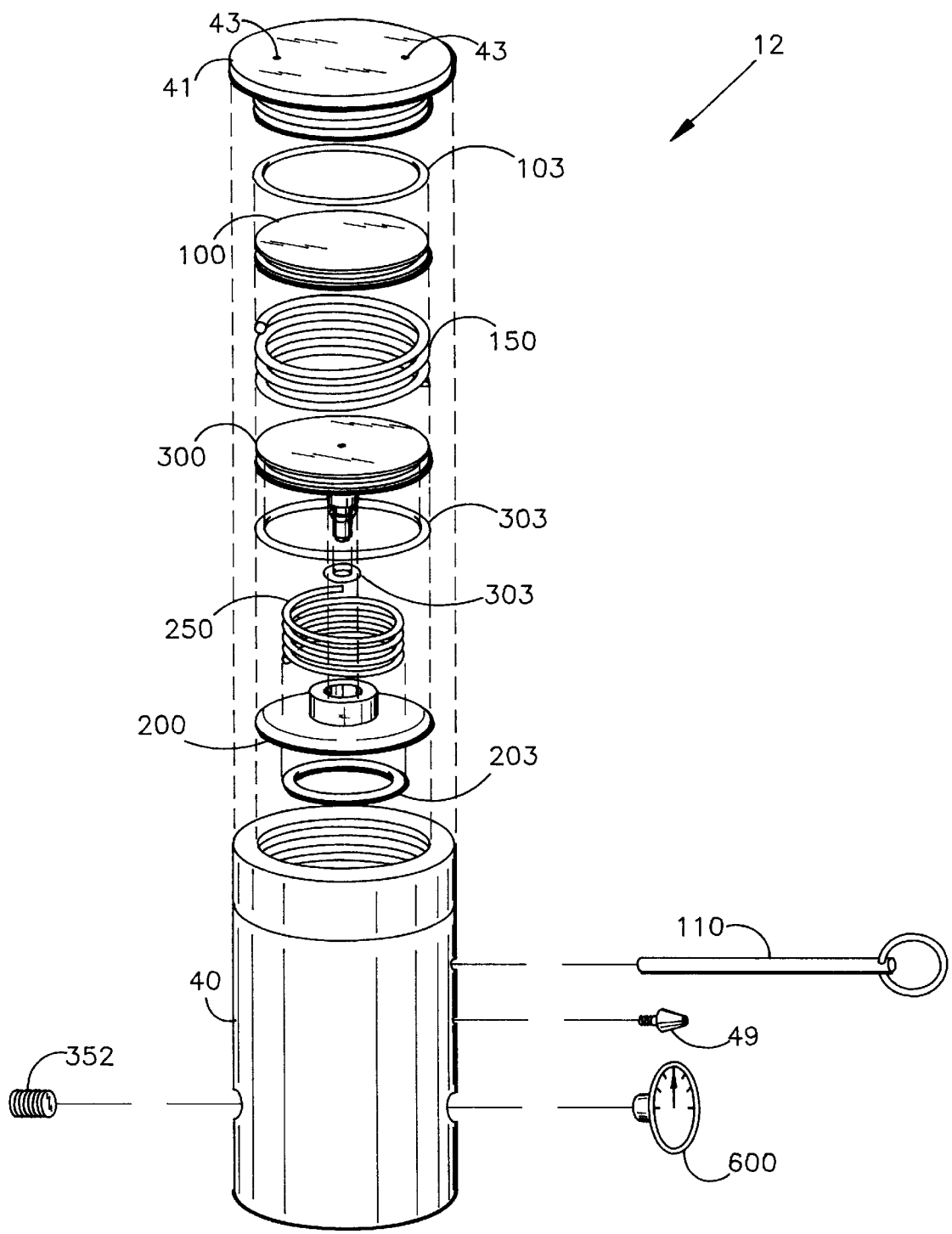
FIG. 3 is an elevated perspective view of an embodiment of the regulator of the invention shown disassembled.

FIGS. 1 and 2 show oxygen delivery system 10 of the invention, and FIG. 3 shows the regulator 12 of the invention. Oxygen d,livery system 10 includes regulator 12 comprising hollow body 40 with a top 42, bottom 44, and interior wall 45. Interior wall 45 has bottom surface 46, and an outlet bore 48 extends through interior wall 45.

Hollow body 40 is formed from a substantially rigid material that is capable of containing elevated gas pressures from 0.0 p.s.i. up to about 3,000 p.s.i. Thus, body 40 may be formed from a thermoplastic or made from metal so long as body 40 is capable of containing pressurized gas from atmospheric pressure to elevated pressure. The inventor's preferred material is anodized aluminum because it has desirable physical and mechanical properties during and after manufacture.

It should be understood that other metals are suitable, such as brass, aluminum composites, and so on but, the inventor's best mode to date is set forth herein. Additionally, body 40 may be coated using a thin surface layer of high purity aluminum to improve both appearance and corrosion resistance.

Cap 41 with access bores 43 is removably secured to top 42 of hollow body 40 in a gas-tight fashion using known means, such as threads. The bottom 44 of body 40 is also secured in a gas-tight fashion to oxygen source 20, which is a small oxygen cylinder having a volume of between about 0.75 liters (L) and 3.0 liters (L) at a pressure of between about 2,500 p.s.i. and 3,000 p.s.i.

First spacer member 100 has o-ring groove 102 in which resides o-ring 103. First spacer member 100 is positioned within body 40 with o-ring 103 sealingly and slidingly engaging interior wall 45. A release pin bore 108 extends transversely through hollow body 40 between top 42 and first spacer member 100 for retaining release pin 110. Release pin 110 has ring 112 for the user to grasp. Release pin 110 defines an interface between cap 41 and first spacer member 100 when pin 110 is in release pin bore 108, as shown in FIG. 1. First spacer member 100 and release pin 110 are formed from the same material(s) as hollow body 40; and thus, o-ring groove 102 is formed using means known by skilled artisans.

A central bore 50 extends axially through bottom 44 for providing fluid communication between oxygen source 20 and the interior of body 40. Central bore 50 has inlet 54 with seat 60 at its upper most end.

Second spacer member 200 has o-ring groove 202 in which resides o-ring 203. Second spacer member 200 is positioned within hollow body 40 with o-ring 203 sealingly engaging bottom surface 46. Second spacer member 200 has an axial bore 210 extending through it for receiving metering member 300 in cylinder-piston fashion.

Metering member 300 has an o-ring groove 302 formed in its upper portion and in its lower portion in which resides an o-ring 303. Metering member 300 is disposed within body 40 between first and second spacer members 100, 200 with the o-ring in its upper portion sealingly and slidingly engaging interior wall 45. The o-ring in the lower portion of metering member 300 sealingly and slidingly engages interior wall of axial bore 210. Metering member 300 is axially slidable between a closed position, as shown in FIG. 1, and an open position, as shown in FIG. 2.

Second spacer member 200 and bottom surface 46 and metering member 300 define an inlet chamber 340. Second spacer member 200 and metering member 300 are formed from the same material(s) as hollow body 40, first spacer member 100, and release pin 110.

With reference to FIG. 2, first spacer member 100 and interior wall 45 and metering member 300 define an outlet chamber 380. Outlet bore 48 extends through interior wall 45 at about the mid portion of body 40 and joins outlet chamber 380 with the exterior of hollow body 40.

A first coil spring 150 is positioned in body 40 for biasing first spacer member 100 and metering member 300 apart, and second coil spring 250 is positioned in body 40 for biasing second spacer member 200 and metering member 300 apart. The respective gauges of coil springs 150, 250 are selected so that in conjunction with fixed-metered outlet 48, as will be described below, oxygen is delivered at a substantially constant pressure of between about 20 p.s.i. and 60 p.s.i.

Hollow body 40 also has relief bore 342 for relieving pressure in inlet chamber 340 and refuel bore 350 extending through interior wall 45 at the lower portion of body 40. Check valve 352 for refueling oxygen source 20 is shown diagramatically and is secured in gas-tight fashion within refuel bore 350. A Schrader valve may be used instead of check valve 352. A pressure gauge 600 for providing a pressure reading of source 20 is coupled to oxygen delivery system 10 using known means.

Referring to FIG. 1, prior to operation, oxygen delivery system 10 is in its closed position. Metering member 300 seats on seat 60, thereby preventing the flow of oxygen from source 20. In operation, the user holds delivery system 10 grasping ring 112 connected to release pin 110. Release pin 110 is pulled from its interface position in bore 108. This actuates regulator 12 and begins a chain of movement within body 40.

Once pin 110 is removed, coil spring 150 urges first spacer member 100 to move upwardly in the direction of top 42 until spacer member 100 abuts the bottom of cap 41, as shown in FIG. 2. This causes coil spring 150 to relax. In response to the relaxing of coil spring 150, coil spring 250 urges metering member 300 upward in the direction of top 42 and into the open position, whereby metering member 300 moves off of seat 60 permitting the flow of oxygen from source 20, through inlet 54, and into inlet chamber 340. Fluid flows consecutively from inlet chamber 340 into outlet chamber 380 via bores 316, 314, as shown in FIG. 2.

When equilibrium of the opposing forces exerted by coil springs 150, 250 on metering member 300 is achieved, the upward movement of metering member 300 stops so that metering member 300 becomes substantially fixed in the open position. As the user breathes, very slight upward and downward movement of metering member 300 occurs. This movement, however, is constantly corrected as a result of the opposing forces exerted on metering member 300 by coil springs 150, 250 to maintain substantially constant fluid flow through regulator 12 until source 20 is empty.

Thus, it should be understood that the tolerances between interior wall 45 and metering member 300, as well as the regulator's specifications, including the thickness of metering member 300 and the gauges of coil springs 150, 250, are predetermined such that upward movement of metering member 300 does not obstruct outlet bore 48.

In this connection, coil spring 150 has a gauge of between about 0.070 and 0.85 inches, and coil spring 250 has a gauge of between about 0.90 and 0.115 inches. These specifications are suitable without excessive experimentation for a regulator like the one disclosed herein having an interior diameter between about 1.00 inches and 1.125 inches.

Additionally, fluid flow out of outlet bore 48 is metered by a predetermined channel 47 formed in a tube fitting 49 that is removably secured within bore 48 in a gas-tight fashion. The above-mentioned tolerances, gauges of coil springs 150,

250 and size of channel 47 together determine the flow rate of fluid from outlet chamber 380. A flow rate of between about 5 liters/minute and 15 liters/minute (L/min.) is desirable.

In the event that pressure in inlet chamber exceeds that which is desirable, relief bore 342 provides pressure relief to system 10. For whatever the reason, as pressure increases within inlet chamber 340, metering member 300 continues moving upwardly against the urging of coil spring 150. Upward movement of metering member 300 continues until the seal formed by the o-ring 303 between metering member 300 and second spacer member 200 is breached permitting fluid to flow into hollow body 40 between metering member 300 and second spacer member 200 and out via relief bore 342. Relief bore 342 provides added safety and makes it possible for regulator 12 to be formed from a broad class of inexpensive thermoplastics that would otherwise be unsuitable for containing pressurized gas.

Oxygen delivery system 10 can be refueled by way of check valve 352 and used repeatedly. The system is easy to operate and does not require a medical technician to hook-up, because mask 500 is held over the user's mouth, and the release pin 110 is simply pulled away from bore 108. Quick-release pin 110 also makes new oxygen delivery system 10 capable of delivering oxygen instantly upon demand from an oxygen source to a human being.

Additionally, the sliding members 100 and 300 that are urged in opposite directions by coil springs 150, 250 preclude the need for complicated pneumatic control systems with valves, solenoids, electronic sensors, and diaphragms that may wear out or fail to operate. Moreover, since all its parts are mechanical oxygen delivery system 10 is inexpensive to manufacture and does not need a source of electricity to operate. Since oxygen delivery device 10 uses a small high-pressure oxygen cylinder 20 as an oxygen source, the system is convenient to carry on the person, too.

While a specific embodiment of the invention has been shown and described herein for purposes of illustration, the protection afforded by any patent which may issue upon this application is not strictly limited to the disclosed embodiment, but extends to all structures and arrangements which fall fairly within the scope of the claims which are appended hereto.

What is claimed is:

1. An emergency oxygen delivery system for delivering oxygen on demand from an oxygen source to a human being via an oxygen mask, the oxygen delivery system comprising:

a regulator device having an inlet and an outlet, said regulator further comprising a hollow body having a top, a cap removably secured to said top, and a bottom, a first spacer member, a second spacer member, and a metering member, positioned in said body, said metering member being axially movable between an open position and a closed position;

means for removably securing said regulator to said oxygen source; and, manual actuating means disposed in said regulator for quickly actuating operation of said regulator, said manual actuating means further comprising a release pin bore for retaining a release pin extending through said regulator, wherein prior to operation, said actuating means maintains said regulator in a closed position, whereby said regulator prevents the flow of oxygen from said oxygen source, and upon actuating said manual actuating means, said regulator assumes an open position, whereby said regulator permits the flow of oxygen from said oxygen source, through said regulator, and to a human being.

2. The oxygen delivery system of claim 1 wherein said release pin bore being formed in said body such that said release pin defines an interface between said cap and said first spacer member when said pin is in said release pin bore.

3. The oxygen delivery system of claim 1 wherein said first spacer member being slidingly and sealingly positioned in said body, said second spacer member being sealingly positioned in said bottom of said body, and said metering member being slidingly and sealingly positioned in said body between said first and second spacer members.

4. The oxygen delivery system of claim 1 wherein said second spacer member having a central bore axially extending therethrough for receiving said metering element.

5. The oxygen delivery system of claim 1 further comprising relief valve means for relieving pressure in said body.

6. The oxygen delivery system of claim 1 further comprising a coil spring positioned in said body for biasing said first spacer member and said metering member apart, a second coil spring positioned in said body for biasing said metering member and said second spacer member apart, a pair of access bores extending through said cap for accessing said first spacer member, wherein said first spacer member being movable downwardly relative to said top so that said release pin may be positioned in said release pin bore, thereby defining said closed position.

7. The oxygen delivery system of claim 1 further comprising refuel valve means for refueling said oxygen source.

* * * * *